United States Patent [19]
Rienstra et al.

[11] Patent Number: 5,039,610
[45] Date of Patent: Aug. 13, 1991

[54] PROCESS FOR REMOVING BACTERIAL ENDOTOXIN FROM GRAM-NEGATIVE POLYSACCHARIDES

[75] Inventors: Mark S. Rienstra; Edgar M. Scattergood, both of Lansdale; Robert D. Sitrin, Lafayette Hill, all of Pa.

[73] Assignee: Merck & Co., Inc., Rahway, N.J.

[21] Appl. No.: 595,737

[22] Filed: Oct. 9, 1990

Related U.S. Application Data

[63] Continuation of Ser. No. 364,929, Jun. 12, 1989, abandoned.

[51] Int. Cl.$^5$ .................... C12P 19; C12P 04; C12P 1/04; C12R 1/21
[52] U.S. Cl. .................... 435/101; 210/601; 210/616; 210/631; 424/88; 424/92; 435/170; 435/262; 435/280; 435/800; 435/803; 435/851; 536/1.1
[58] Field of Search .................... 210/601, 616, 631; 424/88, 92; 435/101, 170, 262, 280, 800, 803, 851; 536/1.1

[56] References Cited

U.S. PATENT DOCUMENTS

| | | | |
|---|---|---|---|
| 4,196,192 | 4/1980 | Kuo | 424/92 |
| 4,220,717 | 9/1980 | Kuo | 435/101 |
| 4,474,758 | 10/1984 | Kuo et al. | 424/92 |
| 4,695,624 | 9/1987 | Marbueg et al. | 536/1.1 |

OTHER PUBLICATIONS

Sweadner et al., Appl. Environ. Micro, 34: 382–385 (1977).
Sands and Chun, J. Biol. Chem. 255: 1221–1226 (1980).
McIntire et al., Biochem. 8: 4063–4066 (1969).
Ribi et al., J. Bact. 92: 1493–1509 (1966).
Feldstine et al., J. Parenter. Drug Assoc. 33: 125–131 (1979).
Berman et al., J. Parenter. Sci. Technol. 41: 158–163 (1987).
Henderson and Beans, Kidney Internatl. 14: 522–525 (1978).
Nelsen, Pharm. Technol. 2: 46–80 (1978).
Gerba et al., Pharm. Technol. 4: 83–89 (1980).
Hou et al., App. Environ. Micro. 40: 892–896 (1980).
Robinson et al., Parneternal Drug Assoc. Philadelphia, pp. 54–69 (1985).
Berger et al., Adv. Chem. Ser. 16: 168–197 (1956).
Gemmell et al., Pharm. J. 154: 126 (1945).
Brindle and Rigby, Pharm. J. 157: 85–86 (1946).
Sawada et al., Appl. Environl. Micro. 51: 813–820 (1986).
Gerba et al., Appl. Environl. Micro. 50: 1375–1377 (1985).
Nolan et al., Proc. Soc. Exptl. Biol. Med. 149: 766–770 (1975).

*Primary Examiner*—Herbert J. Lilling
*Attorney, Agent, or Firm*—Hesna J. Pfeiffer; Richard S. Parr

[57] ABSTRACT

A process for removing endotoxin from Gram-negative polysaccharides such as polyribosylribitol phosphate by solubilizing polysaccharide-containing powder derived from Gram-negative bacteria fermentation broth to provide a divalent counter ion for endotoxin and adding alcohol incrementally to induce lipopolysaccharide precipitation, and mixing material resulting from the alcohol addition with a nonionic resin, a detergent and a chelating agent.

6 Claims, 4 Drawing Sheets

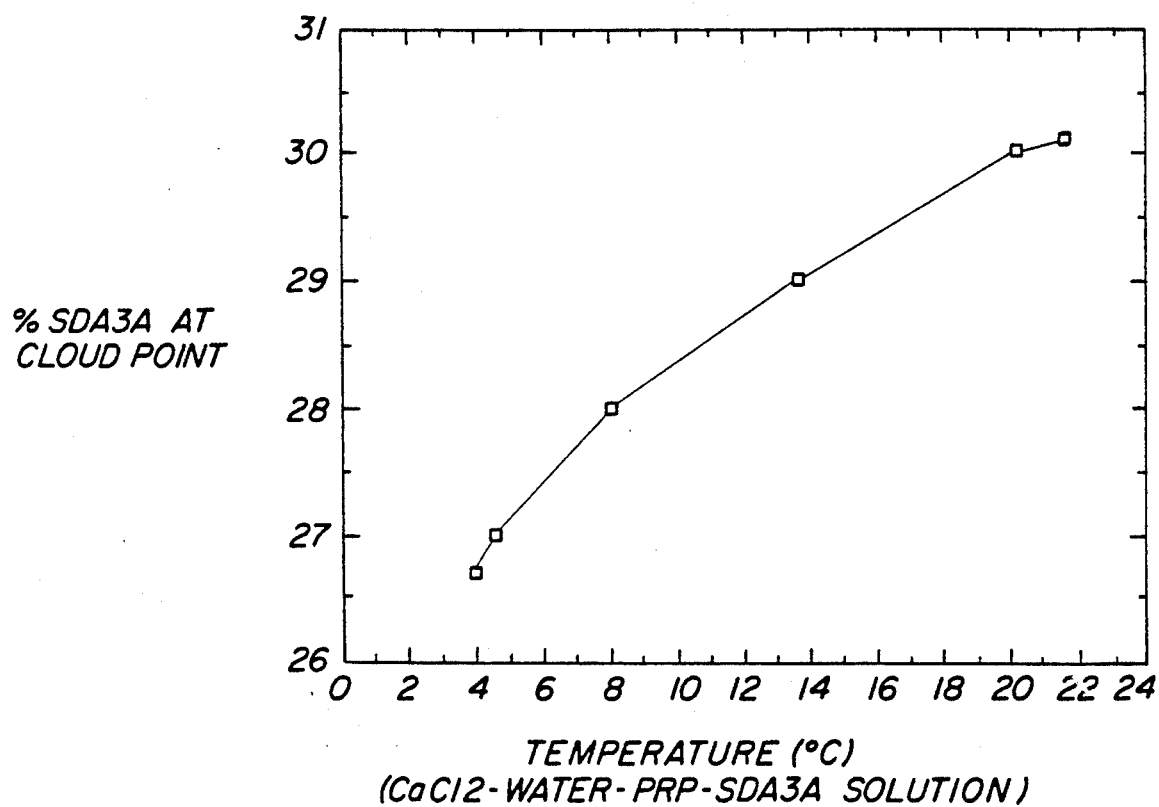

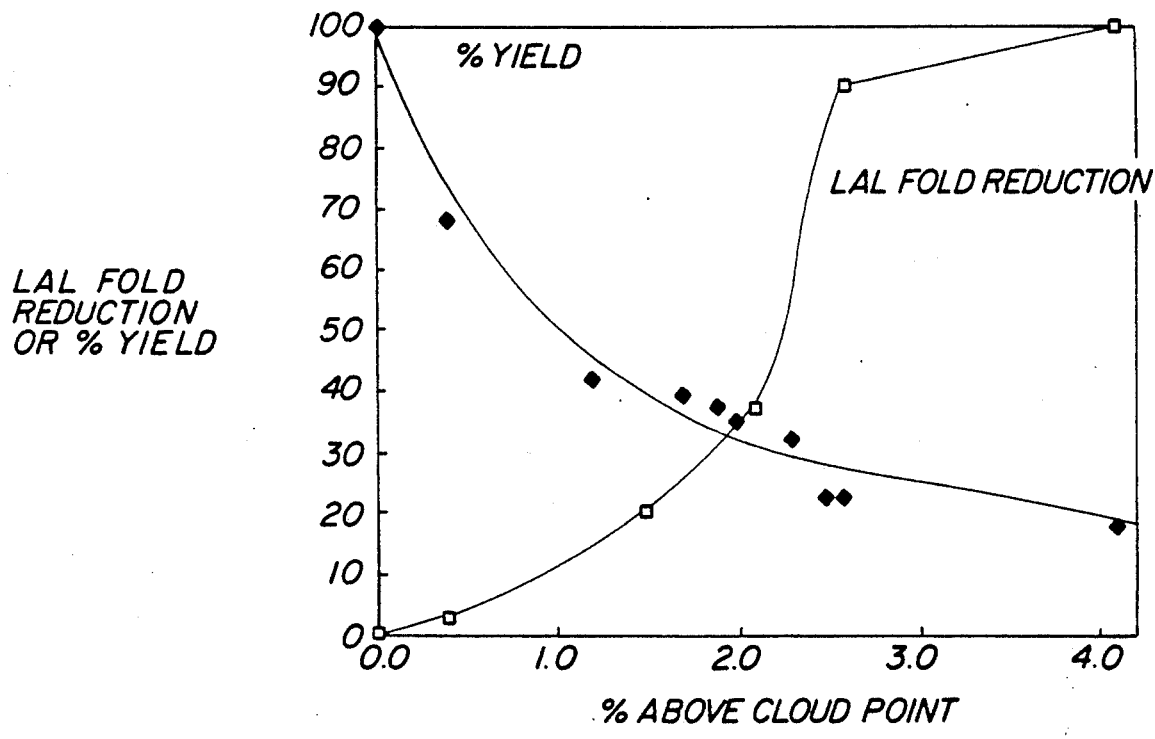

PROCESS FOR REMOVING BACTERIAL ENDOTOXIN FROM GRAM-NEGATIVE POLYSACCHARIDES

This is a continuation of application Ser. No. 364,929, filed June 12, 1989, now abandoned.

BACKGROUND OF THE INVENTION

The invention is a process for removing bacterial endotoxin from Gram-negative polysaccharides without incurring substantial loss of polysaccharide.

Bacterial endotoxin is a potent pyrogen that can often produce fever reactions when administered to patients. Endotoxin is an integral component of the outer cell surface of Gram-negative bacteria. It exists in its natural state as a complex of lipid, carbohydrate and protein. When highly purified, endotoxin does not contain protein, and by its chemical composition is referred to as a lipopolysaccharide (see Weary and Pearson, Bio. Pharm. April (1988) pp. 22-29).

The outer-wall layer of Gram-negative bacteria serves as an outer barrier through which materials must penetrate if they are to reach the cell. It is selectively permeable. Generally, endotoxin is released in large amounts only when the cell wall is lysed.

Removal of contaminating endotoxin from Gram-negative polysaccharides is important when the polysaccharide is to be administered to humans. Endotoxins in large quantities can cause shock, severe diarrhea, fever and leukopenia followed by leukocytosis, and can elicit the Shwartzman and Sanarelli-Shwartzman and phenomena.

U.S. Pat. No. 4,695,624, issued to Marburg et al., describes covalently-modified polyanionic bacterial polysaccharides, stable covalent conjugates of these polysaccharides with immunogenic proteins, and methods of preparing the polysaccharides and conjugates and of confirming covalency. The patent describes purification of the polysaccharide in Example 1, beginning in column 14. After fermentation, inactivation and cell removal, the resulting product undergoes a series of cold ethanol fractionations. Following phenol extraction are diafiltration, ethanol precipitation, ultracentrifugation in ethanol, and collection of the finished product.

Frequently, the amount of contaminating endotoxin remaining after the above-described procedure is higher then desired.

Methods for removing endotoxin which are known in the art are described by Weary and Pearson (ibid): rinsing with nonpyrogenic solution (Feldstine et al., *J. Parenter. Drug Assoc.*, 33, p. 125 (1979) and Berman et al., *J. Parenter. Sci. Technol.*, 41, p. 158 (1987); distillation; ultrafiltration using membranes rated by molecular weight exclusion (Sweadner et al., *Appl. Environ. Microbiol.*, 34, p. 382 (1977) and Henderson et al., *Kidney Int.*, 14, p. 522 (1978); reverse osmosis using thin cellulose acetate or polyamide materials (Nelson, *Pharm. Technol.*, 2, p. 46 (1978); electrostatic attraction (Gerba et al., *Pharm Technol.*, 4, p. 83 (1980) and Hou et al., *Appl. Environ. Microbiol.*, 40, p. 892 (1980); hydrophobic attraction using aliphatic polymers (Robinson et al., in *Depyrogenation* (Parenteral Drug Association, Philadelphia (1985), pp. 54-69); adsorption using activated carbon (Berger et al., *Adv. Chem. Ser.*, 16, p. 169 (1956), Gemmell et al., *Pharm J.*, 154, p. 126 (1945), and Brindle et al., *Pharm. J.*, 157, p. 85 (1946); and affinity chromatography (Soter, Bio/Technology, 12, p. 1035 (1984).

Sawada et al., *Applied and Environmental Microbiology*, April 1986, pp. 813-820, describe removal of endotoxin from water by microfiltration through a microporous polyethylene-hollow-fiber membrane. Gerba et al., *Applied and Environmental Microbiology*, December 1985, pp. 1375-1377, describe endotoxin removal from various solutions using charged nylon and cellulose-diatomaceous earth filters. Nolan et al., *Proceeding of the Society for Experimental Biology and Medicine*, vol. 149, pp. 766-770 (1975), describe endotoxin binding by charged and uncharged resins.

Sweadner, K. et al., *Applied and Environmental Microbiology*, Vol. 34, pp. 382-385 (1977) explain that lipopolysaccharide often exist in an aggregated state, and that dissociating the lipopolysaccharide with detergent or chelating agents can facilitate its removal from aqueous solutions by filtration. Shands, J. et al., *J. Biological Chemistry*, Vol. 255, pp. 1221-1226 (1980), show that lipopolysaccharide is associated with divalent cations, and that dispersion of Gram-negative lipopolysaccharides can be achieved using deoxycholate.

McIntire, et al, *Biochemistry*, Vol. 8, No. 10, pp. 4063-4066 (1969) describes reversible inactivation, by sodium deoxycholate, of *Escherichia coli* lipopolysaccharide. Ribi, et al., *Journal of Bacteriology*, Vol. 92, No. 5, pp. 1493-1509 (1966) described physical and biological properties of endotoxin treated with sodium deoxycholate.

It is a purpose of the present invention to provide an effective method of obtaining Gram-negative polysaccharide mixtures having low or negligable levels of endotoxin, without suffering substantial loss of polysaccharide.

It is also a purpose of the present invention to provide a process for eliminating endotoxin from a solution of bacterial polysaccharide while minimizing the removal of bacterial polysaccharides and other desired species.

SUMMARY OF THE INVENTION

The invention is a process for removing endotoxin from Gram-negative polysaccharides such as polyribosylribitol phosphate (PRP) which comprises:

(a) growing Gram-negative bacteria in fermentation broth, releasing polysaccharide into the broth, and adding alcohol to the broth to remove impurities by precipitation;

(b) isolating the remaining high molecular weight species and resolubilizing them in phenol and extracting other impurities;

(c) centrifuging remaining high molecular weight species and resolubilizing in a counter ion solution;

(d) adding alcohol to the solution, cooling the solution and thereafter incrementally adding alcohol to achieve lipopolysaccharide precipitation and lipopolysaccharide/polysaccharide precipitation by selective alcohol fractionation; and (e) mixing lipopolysaccharide-and polysaccharide-containing material resulting from the alcohol addition with a nonionic resin, a detergent and a chelating agent, to remove lipopolysaccharide by resin elimination.

Preferably, the initial addition of alcohol and the temperature after cooling in step (d) results in an alcohol concentration which is up to 2%, preferably between 0.5-1% below the alcohol concentration at the cloud point. Incremental alcohol addition is preferably a sequential addition of about 0.2% at a time until a two-fold increase in turbidity occurs, at which time the cloud point has been reached. The cloud point is the percentage of alcohol when endotoxin and polysaccharide start to precipitate, causing turbidity. After the cloud point has been reached, an additional amount of alcohol is added which results in precipitation of most of the endotoxin with some polysaccharide.

The counter ion is preferably divalent, but may be monovalent.

Various alcohols may be successfully used during endotoxin removal. Suitable alcohols include denatured ethanol (SDA3A, which is 4.7% MeOH, 88.1% EtOH, 7.2% $H_2O$), 95% EtOH, absolute EtOH, isopropanol, and other alcohols having 1 to 4 carbons which precipitate endotoxin.

Material mixed with resin, detergent and chelating agent may be powder derived from the operation in step (d). Such powder is obtained by drying the precipitate resulting from step (d). It is comprised of polysaccharide and lipopolysaccharide.

Material mixed with resin, detergent and chelating agent may also be a solution obtained from the operation in step (d) which comprises polysaccharide and lipopolysaccharide.

Subjecting these materials to treatment with resin, detergent and chelating agent removes substantially all lipopolysaccharide and improves the overall yield of purified polysaccharide which would otherwise be obtained using only incremental alcohol fractionation. Furthermore, use of the resin elimination methodology allows for manipulation of the amounts of non-polysaccharide and nonlipopolysaccharide species in the finished product, while achieving endotoxin removal.

After treatment of the material in step (e), the resin is removed and the polysaccharide precipitated from solution with alcohol. The precipitate is centrifuged, the pellet triturated with alcohol and the resulting product dried to form a powder.

Removal of lipopolysaccharides by the process of selective alcohol fractionation in combination with resin elimination is useful for manipulating the amounts of materials other than polysaccharides and lipopolysaccharides in the final product. Selective alcohol fractionation removes materials primarily on the basis of molecular weight. Increasing concentrations of alcohol result in elimination of species of decreasing molecular weight. Removal of lipopolysaccharides using resin depends on the ability of the resin to recognize lipopolysaccharide structures and eliminate species of that nature from solution. Therefore, the process of the present invention is particularly advantageous for minimizing undesirable eliminations of components other than polysaccharides and lipopolysaccharides. Amounts of components other than polysaccharides and lipoplysacchardes can be regulated by utilizing either the selective alcohol fractionation or resin elimination to a greater extent while obtaining the desirable result of essentially eliminating endotoxin from the final product.

The following abbreviations are used in the description of the present invention:

PRP—polyribosylribitol phosphate, and *H. influenzae* type b capsular polysaccharide.

LAL test value—limulus ameobocyte lysate test value, which is an indication of endotoxin level in the end-product.

LPS—lipopolysaccharide, which is the general structure of endotoxin when it is apart from the outer cell surface of Gram-negative bacteria.

EU/mcg—Endotoxin units (a measure of LPS) per microgram PRP.

BRIEF DESCRIPTION OF THE DRAWINGS

FIG. 3. Plot of alcohol at cloud point versus temperature of PRP powder solution.

FIG. 4. LAL fold reduction and percent yield.

DETAILED DESCRIPTION OF THE INVENTION

Figure 1:
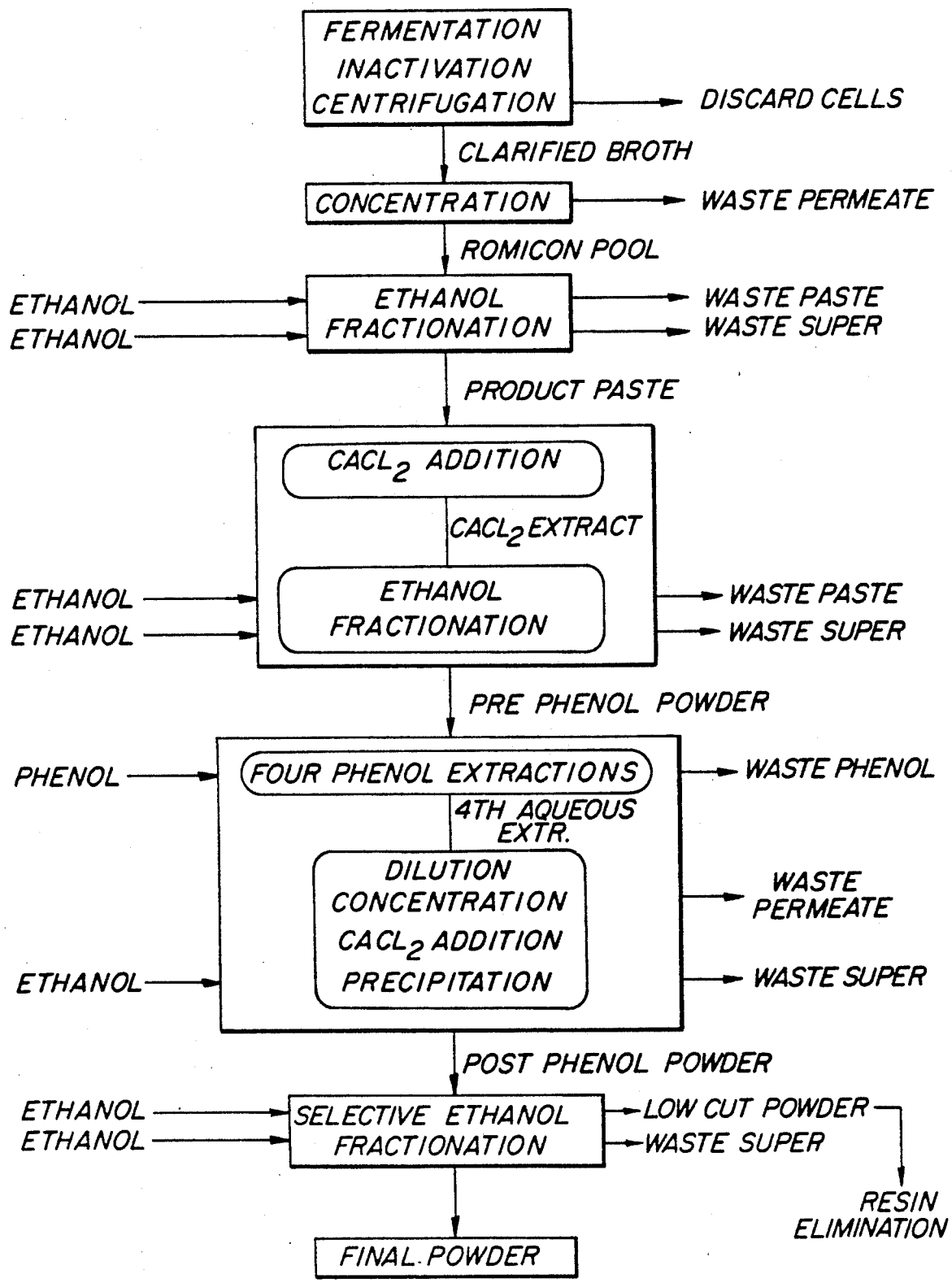
FIG. 1. Endotoxin removal using alcohol fractionation and resin elimination.

In one embodiment of the invention, a production fermenter containing complete Haemophilus medium with an antifoaming agent is inoculated with the seed culture. The fermenter is maintained at $37°\pm3°$ C. for a minimum of twelve hours with moderate aeration and agitation. The *H. influenzae* type b culture is inactivated after the fermentation is completed by addition of thimerosal under agitation. Cell debris, media components and other impurities are removed by centrifugation or filtration and discarded. The culture supernatant is concentrated by ultrafiltration and additional impurities are removed by alcohol fractionation.

The high molecular weight species are dissolved in calcium chloride solution and a minimum of one additional alcohol fractionation is completed as described above to remove additional impurities. The second alcohol precipitate is collected by centrifugation and a dry powder is obtained by resuspending the precipitate in absolute ethanol followed by filtration, acetone wash and drying.

The powder is dissolved in sodium acetate solution and extracted several times with phenol to remove impurities. The aqueous solution containing polysaccharide is diafiltered with water to remove phenol. Calcium chloride solution is added to the solution and high molecular weight species are precipitated with alcohol and collected by centrifugation. The post phenol powder is resolubilized in calcium chloride solution and is then subjected to selective alcohol fractionation.

Selective alcohol fractionation is an effective process for reducing the level of endotoxin to the point where it meets product specification, while minimizing the loss of polysaccharide from solution. By changing the alcohol concentration, different molecular weight species become insoluble and precipitate out of solution. Increasing alcohol concentration precipitates species of decreasing molecular weight. Ethanol is incrementally added, thereby increasing ethanol concentration towards the cloud point. When the cloud point is reached, polysaccharide and LPS precipitate. Because it can be advantageous to recover the polysaccharide precipitating with the lipopolysaccharide, the combination is dried to a "low cut" powder and later treated by the resin elimination method. Lipopolysaccharide is precipitated along with some polysaccharide, leaving polysaccharide in solution essentially unaccompanied by lipopolysaccharide.

The precipitating material which contains lipopolysaccharides, polysaccharides and other species, such as proteins and lipids, is combined with a resin, a detergent and a chelating agent to remove polysaccharide. The material is first combined with the detergent and chelating agent under basic pH, and resin beads are then added to and mixed with the solution in an orbital shaker for several hours below room temperature. The beads are then removed from solution, and the filtrate is diafiltered using hollow fiber membranes to remove detergent and chelating agent. Retentate is recovered and calcium chloride added. The polysaccharide is precipitated from solution with alcohol. The precipitate is centrifuged and the pellet is triturated with alcohol and acetone. The resulting product is vacuum dried. This process reduces endotoxin level without significant loss of polysaccharide.

The process of the present invention, therefore, accomplishes removal of impurities such as lipopolysaccharides from fermentation products of Gram-negative bacteria by selective alcohol fractionation followed by treatment with resin, a detergent and a chelating agent.

Although sodium citrate is a preferred chelating agent, other chelating agents which are capable of acting on divalent calcium ions present in the solution, and which are capable of serving as a buffer for maintaining basic pH are suitable. Other suitable chelating agents include ethylenediaminetetraacetic acids such as disodium ethylenediaminetetraacetic acid. Preferably, the amount of chelating agent is between about 1% and about 10%, more preferably between about 2% and about 7% and even more preferably about 6%.

Although deoxycholate is a preferred detergent, other detergents which are capable of breaking aggregated lipopolysaccharide are suitable. Suitable detergents include Triton X-100, CHAPS, sodium dodecyl sulfate, and sodium lauryl sulfate. Preferably, the amount of detergent is between about 0.1% and about 2.0%, more preferably between about 0.2% and about 1.0% and even more preferably about 0.75%.

Nonionic resins which bind to lipopolysaccharide, which do not bind to polysaccharides, and which are useful in the present invention include but are not limited to Borate Avidgel (Amicon), Amberlite XAD and Amberchrome (Rohm & Haas), Octyl Cellulose (Phoenix Chem.), Silicon C8 (Baker), SP207 and HP20 (Mitsubishi Chem.). Of these resins, HP20 is preferred because of lipopolysaccharide reduction, ease of use, availability, cost, and its propensity to avoid binding to polysaccharides. Preferably the resin is washed prior to use with pyrogen free water. More preferably, the resin is washed prior to use with acid solution, an alkali solution, or a polar solvent (e.g. ethanol or methanol) and then with pyrogen free water.

In a preferred embodiment of the invention, powder obtained by drying the precipitate resulting from step (d), which comprises H. influenzae, type b bacterium polyribosylribitol phosphate, lipopolysacchride and various lipids and proteins, is mixed with HP20 (highly porous styrene and divinylbenzene copolymer) resin, sodium citrate, and deoxycholate, under suitable conditions. The lipopolysaccharide binds to the resin which is thereafter removed. The filtrate is diafiltered, the retentate recovered, and polyribosylribitol phosphate precipitated from solution with alcohol. The precipitate is centrifuged, the resulting pellet triturated with ethanol and acetone, and resulting solution vacuum dried. In the process, the detergent breaks the association of the aggregated lipopolysaccharide. The chelating agent ties up the divalent calcium ions so the vesicular structure of the lipopolysaccharide cannot be maintained, and also serves as a buffer to maintain the pH above 8, mainly to prevent detergent gelation. The lipopolysaccharide is then able to bind hydrophobically to the resin. The PRP, which does not bind to the resin, remains free in solution and can be recovered in the filtrate. The membrane diafiltrations which follow remove the detergent and chelating agent from the solution, and the PRP is then precipitated and dried in a typical manner.

Polysaccharide solutions from which endotoxin is removed in accordance with the present invention may contain any bacterial polysaccharides with acid groups, but are not intended to be limited to any particular types. Examples of such bacterial polysaccharides include *Haemophilus influenzae* (H. flu) type b polysaccharide; *Neisseria meningitidis* (meningococcal) groups A, B, C, X, Y, W135 and 29E polysaccharides; and *Escherichia coli* K1, K12, K13, K92 and K100 polysaccharides. Particularly preferred polysaccharides, however, are those capsular polysaccharides selected from the group consisting of H. flu b polysaccharide, such as described in Rosenberg et al., *J. Biol. Chem.*, 236, pp. 2845-2849 (1961) and Zamenhof et al., *J. Biol. Chem.*, 203, pp. 695-704 (1953).

*H. influenzae* type b polyribosylribitol phosphate, shown below,

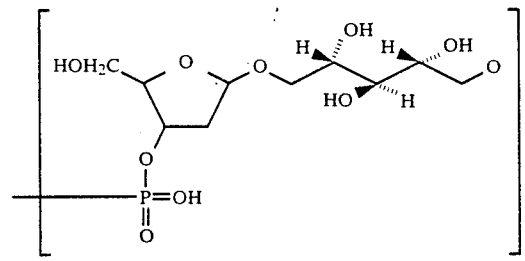

may be prepared for use in protein-polysaccharide conjugates such as those described in Marburg et al., U.S. Pat. No. 4,695,624.

The limulus ameobocyte lysate (LAL) test, described in "Guideline on validation on the LAL test as an end-product endotoxin test for human and animal parenteral drugs, biological products, and medical devices." U.S. Department of Health and Human Services, December 1987, is used to determine endotoxin levels.

EXAMPLE 1

Endotoxin Removing Using Alcohol Fractionation and Resin Elimination

A schematic representation of the process followed in this example is shown in FIG. 1.

In the selective ethanol fractionation step, the lipopolysaccharide was precipitated as alcohol concentration increased, along with some polysaccharide, leaving polysaccharide in solution with reduced lipopolysaccharide. Precipitate containing lipopolysaccharide along with polysaccharide is known as the "low-cut" or "pre-cut". The pre-cut material is subjected to further endotoxin removal using resin, detergent, and chelating agent (as described later).

Incremental addition of alcohol is an effective process for reducing the level of endotoxin to the point where it meets product specification, while minimizing the loss of polysaccharide from solution. By changing the alcohol concentration, different molecular weight species become insoluble and precipitate out of solution. Increasing alcohol concentration precipitates species of decreasing molecular weight.

Thus, the solution from which endotoxin is to be removed is cooled and a salt such as $CaCl_2$ or NaCl is added. Chilled alcohol, such as SDA3A, is added to achieve a concentration slightly below (about 0.5–1.0%) less than the cloud point (see Graph 2). Sequential addition thereafter of about 0.2% alcohol at a time is performed until a two-fold increase in turbidity occurs, at which point the cloud point has been reached.

Products obtained from Tests a, c, d, and e in Table 1 show dramatic reductions of endotoxin level following the process of the invention. Test e, which had an unacceptably high level of endotoxin, was treated a second time by selective ethanol fractionation, the results of which are shown in test f.

TABLE 1

| | Endotoxin Reduction Using Selective Alcohol Fractionation | | | | | |
|---|---|---|---|---|---|---|
| | Test (EU/mcg) | | | | | |
| | a | b | c | d | e | f |
| Pre-phenol Powder | 750 | 650 | 530 | 600 | 780 | — |
| Post-phenol Powder | 45 | 140 | 60 | 60 | 135 | — |
| Low cut Powder | 30 | 600 | 340 | 30 | 300 | — |
| Powder After Selective Alcohol Fractionation | 1.5 | 0.9 | 1.4 | 0.4 | 2.8 | 0.09 |

To accomplish the selective alcohol fractionation, the post-phenol powder was solubilized at 2.5 g/L in a 0.05M $CaCl_2$ solution to provide a divalent counter ion for both endotoxin and PRP. Alcohol was then added to 26% (v/v). After the temperature equilibrated to a constant value in the 2° to 4° C. range, alcohol was added incrementally until the PRP begins to precipitate (cloud point), causing turbidity as monitored by a turbidity probe.

Graph 1 is a plot of % alcohol at the cloud point versus the temperature of a PRP powder solution. The % alcohol needed to reach the cloud point at 6° C. was 27.4% but for the 4° C. only 26.7% was required. This seemingly small increase corresponded to 700 ml for a 100 L scale run. The final powder yield decreased as the difference between Low Cut Alcohol percent and Cloud Point percent increased. Graph 2 shows that an increase in alcohol content of 1% from the cloud point alcohol concentration removed 50% of the PRP. Endotoxin reduction, as measured by LAL, was about ten fold. Therefore, alcohol addition of 1% was not sufficient to reduce the endotoxin to a level of 3 EU/mcg when the starting LAL was greater than 30 EU/mcg.

After the low cut alcohol was added, the solution was immediately centrifuged to remove low cut precipitate. Additional alcohol was added to the supernatant to 38% (v/v). The desired precipitate was collected via settling and/or centrifugation and dried to the final powder. Typical recoveries for this step at 1.2–2.0% above the cloud point were 30–40% of the post-phenol powder or 13–18% of the amount from the fermentor.

The selective alcohol fractionation procedure can be repeated if the final powder does not meet the pyrogen specification. For reprocessing, the alcohol concentration was increased 0.2% above the low cut alcohol percentage. The yield was 78% and the endotoxin level was reduced from 2.8 to 0.09 EU/mcg.

Endotoxin Removal Using Resin, Detergent and Chelating Agent

Figure 2:
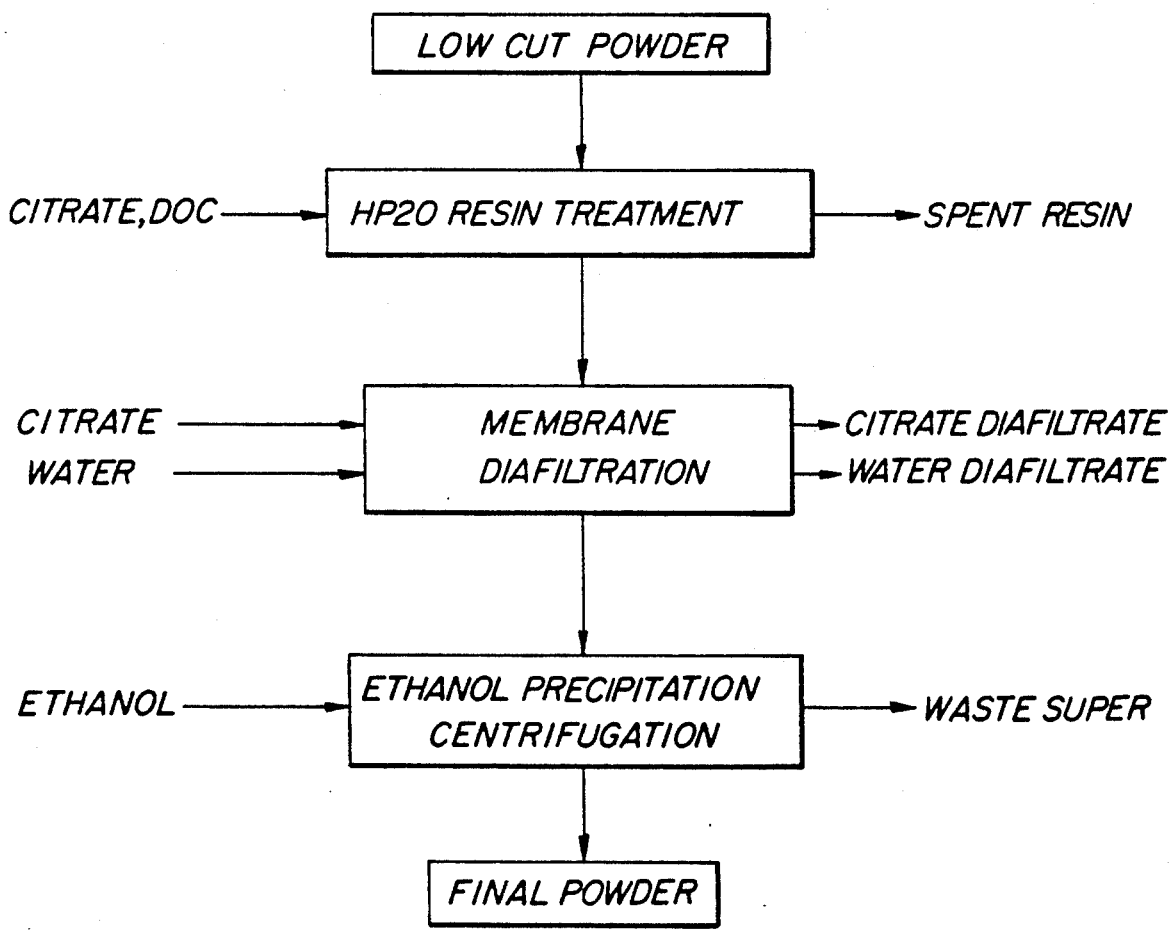
FIG. 2. Endotoxin removal using resin, detergent and chelating agent.

The pre-cut or low-cut material obtained after performing the selective ethanol fractionation step, containing precipitated lipopolysaccharide and polyribosylribitol phosphate, was further treated by mixing with HP20 resin, deoxycholate and sodium citrate. This treatment removes substantial quantities of lipopolysaccharide without significantly affecting the level of desirable polyribosylribitol phosphate contained in the low cut material. The filtrate is diafiltered with a hollow fiber membrane, the retentate recovered, and polyribosylribtol phosphate precipitated from solution with ethanol. The precipitate is centrifuged and resulting pellet triturated with ethanol and acetone. The resulting solution is then vacuum dried, see FIG. 2.

0.5% sodium deoxycholate and 3% sodium citrate were mixed with the lipopolysaccharide-polysaccharide mixture at pH 8–9. HP20 resin was added at 30 grams resin per gram polysaccharide (the resin was washed prior to use with pyrogen free water). The loose beads were mixed with the solution on an orbital shaker for 3 hours at 4° C. After mixing, the beads are removed from the solution in a stainless steel filter funnel. Filtrate is then diafiltered in an Amicon H1P30-20 hollow fiber cartridge (0.06$M^2$ surface area) vs. 5 vol. of 1.5% citrate followed by 10 vol. of pyrogen free water, maintaining an estimated polysaccharide concentration of $\leq 2.5$ mg/ml, to remove detergent and chelating agent. The retentate is recovered and 2M calcium chloride is added to achieve a final calcium chloride concentration of 0.05M. Polysaccharide is precipitated from solution with excess 95% ethanol. The precipitate is centrifuged at 13,000 x g for 30 minutes, the pellet triturated with absolute ethanol and acetone, and then vacuum dried. The final powder is transferred to a sample container and frozen at −70° C.

Material treated with resin showed the following reductions of endotoxin levels and polysaccharide levels:

| LAL test value EU/mcg | A | B | C |
|---|---|---|---|
| initial | 100 | 100 | 100 |
| final powder | 0.06 | 0.03 | 0.06 |

| Polysaccharide level (%) | | | |
|---|---|---|---|
| initial | 100 | 100 | 100 |
| final powder | 90 | 100 | 92 |

EXAMPLES 2, 3, 4, 5, 6, 7 AND 8

Following the procedure for endotoxin removal described in Example 1, maintaining a concentration of sodium deoxycholate of 0.5%, and beginning with powder having LAL of 60 EU/mcg, we obtained considerable reduction in LPS with these varying amounts of sodium citrate:

| | % Sodium Citrate | LAL (EU/mcg) | |
|---|---|---|---|
| | | Start | Finish |
| Example 2 | 2 | 60 | 30 |
| Example 3 | 3 | 60 | 6 |
| Example 4 | 4 | 60 | 0.6 |

-continued

|  | % Sodium Citrate | LAL (EU/mcg) Start | Finish |
|---|---|---|---|
| Example 5 | 5 | 60 | 0.6 |
| Example 6 | 6 | 60 | 0.15 |
| Example 7 | 7 | 60 | 0.6 |
| Example 8 | 8 | 60 | 0.6 |

EXAMPLES 9, 10 AND 11

Following the procedure for endotoxin removal described in Example 1, maintaining a concentration of sodium citrate of 6%, and beginning with powder having LPS of 60 UE/mcg, we obtained considerable reduction in LPS with these varying amounts of deoxycholate:

|  | % Sodium Deoxycholate | LAL (EU/mcg) Start | Finish |
|---|---|---|---|
| Example 9 | 0.25 | 60 | 15 |
| Example 6 | 0.5 | 60 | 0.15 |
| Example 10 | 0.75 | 60 | 0.006 |
| Example 11 | 1.0 | 60 | 0.6 |

EXAMPLES 12, 13, 14, 15 AND 16

Following the general procedures in Example 1, these examples include description or process variations within the invention.

|  | Process Variation |
|---|---|
| Example 12 | After treatment in accordance with Example 1, the procedure is repeated. |
| Example 13 | After treatment according to Example 3, filtrate is diafiltered with 3% sodium citrate, sodium deoxycholate is added, and the solution treated for three additional hours with the original HP-20 resin. |
| Example 14 | After three hours of HP-20 treatment according to Example 3, an equal volume of 3% citrate with 0.5% sodium deoxycholate was added to the mixture and resin treatment continued for another three hours. |
| Example 15 | After three hours according to Example 3, sodium citrate with 0.5% sodium deoxycholate powder were added and the resin treatment continued for another three hours. |
| Example 16 a,b | (a) Six percent sodium citrate with 0.5% sodium deoxycholate or (b) 6% sodium citrate with 1% sodium deoxycholate was used for three hours. |

EXAMPLE 17

All of the process steps of Example 1 are used, except that the resin is packed in a column, rather than mixed in batch with PRP. Thus, the PRP is dissolved in a solution of sodium citrate and sodium deoxycholate, and the resulting solution is passed through the column. The resulting product is similar to that obtained on Example 1.

EXAMPLE 18

All of the process steps of Example 1 are repeated, except that the resin is packed in a cartridge, rather than mixed in batch with PRP. Thus, the PRP is dissolved in a solution of sodium citrate and sodium deoxycholate, and the resulting solution is passed through the cartridge. The resulting product is similar to that obtained in Example 1.

The polysaccharide product resulting from the endotoxin removal procedure of the invention is especially useful where endotoxin-free polysaccharide such as polyribosylribitol phosphate is desirable. It readily conjugates to proteins, e.g. immunogenic proteins, such as in the manner described in Marburg et al. (ibid). The conjugates are stable polysaccharide-protein conjugates, coupled through bigeneric spacers containing a thioether group and primary amine, which form hydrolytically-labile covalent bonds with the polysaccharide and the protein. Exemplary conjugates are those which may be represented by the formulae, Ps-A-E-S-B-Pro or Ps-A'-S-E'-B'-Pro, wherein Ps represents a polysaccharide; Pro represents a bacterial protein; and A-E-S-B and A'-S-E'-B' constitute bigeneric spaces which contain hydrolytically-stable covalent thioether bonds, and which form covalent bonds (such as hydrolytically-labile ester or amide bonds) with the macromolecules, Pro and Ps. The specific definitions of A,E,S,B,A',E' and B' are presented in Marburg et al. the contents of which are hereby incorporated by reference. Procedures for preparing polysaccharides and proteins for conjugation, performing conjugation, and determining conjugation are described in the patent.

What is claimed is:

1. A method of removing endotoxin from a Gram-negative bacteria fermentation product with comprises the steps of:
   (a) growing endotoxin containing Gram-negative bacteria in fermentation broth, and adding alcohol to the broth to remove impurities by precipitation;
   (b) isolating the high molecular weight species and resolubilizing them in phenol and extracting the impurities;
   (c) centrifuging the remaining high molecular weight species and resolubilizing in a divalent counter ion in solution;
   (d) adding alcohol to the solution, cooling the solution, and therafter incrementally adding alcohol to achieve lipopolysaccharide/polysaccharide precipitation; and
   (e) mixing the lipopolysaccharide and polysaccharide-containing precipitate of step (d) with a nonionic resin, a detergent and a chelating agent to remove endotoxin.

2. A method of claim 1 wherein the initial addition of alcohol and temperature after cooling in step (d) results in an alcohol concentration which is up to 2% below the alcohol concentration at the cloud point.

3. The method of claim 1 wherein the polysaccharide is polyribosylribitol phosphate.

4. A method of claim 1 wherein the chelating agent is sodium citrate.

5. A method of claim 1 wherein the detergent is deoxycholate.

6. The method of claim 1 wherein the resin is a highly porous styrene and divinylbenzene copolymer.

* * * * *